United States Patent
Westman et al.

(10) Patent No.: US 12,157,744 B2
(45) Date of Patent: *Dec. 3, 2024

(54) COMPOUNDS AND METHODS OF THEIR MANUFACTURING

(71) Applicant: DICOT PHARMA AB, Uppsala (SE)

(72) Inventors: Jacob Westman, Järlåsa (SE); Catarina Malmberg, Uppsala (SE)

(73) Assignee: DICOT PHARMA AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 18/469,860

(22) Filed: Sep. 19, 2023

(65) Prior Publication Data

US 2024/0124480 A1 Apr. 18, 2024

(30) Foreign Application Priority Data

Sep. 30, 2022 (SE) .................... 2251130-7

(51) Int. Cl.
*C07D 493/18* (2006.01)
(52) U.S. Cl.
CPC ................. *C07D 493/18* (2013.01)
(58) Field of Classification Search
CPC .................................. C07D 493/18
See application file for complete search history.

(56) References Cited

FOREIGN PATENT DOCUMENTS

| WO | 2008/145996 A2 | 12/2008 |
| WO | WO 2013/110744 | 8/2013 |

OTHER PUBLICATIONS

U.S. Appl. No. 18/496,043 (2022).*
Ansell, S.M. et al, Limonoids from the seed of Entandrophragma caudatum, Phytochemistry, 1998, 1218-1220.
Peng, Jun-Lin et al, Two new phragmalin-type limonoids from stems of Chukrasia tabularis, Phytochemistry Letters, 2015, 15, 230-233.
Peng, Jun-Lin et al, New Phragmalin-type limonoids from Chukrasia tabularis and their alfa-glucosidase inhibitory activity, Molecules, 2016, 21, 58, 1-12.
Swedish Office Action and Search Report issued on May 2, 2023 for Swedish Application No. 2251130-7. (6 pages).
Fossen et al., "New Polyfunctional Phragmalin Limonoids from Neobeguea mahafalensis," Planta Med 82:1087-1095 (2016).
Razafimahefa et al., "Libiguins A and B: Novel Phragmalin Limonoids Isolated from Neobeguea mahafalensis Causing Profound Enhancement of Sexual Activity," Planta Med 80:306-314 (2014).
Grigorjeva et al., "Semisynthesis of Libiguin A and Its Analogues by Trans-Lactonization of Phragmalin," J. Org. Chem. 79:4148-4153 (2014).

\* cited by examiner

*Primary Examiner* — Paul V Ward
(74) *Attorney, Agent, or Firm* — Troutman Pepper Hamilton Sanders LLP (Rochester)

(57) ABSTRACT

The present document is directed to methods for producing therapeutically active limonoids as well as new limonoid-type compounds.

12 Claims, 6 Drawing Sheets

Formula Ia

Formula Ib

COMPOUNDS AND METHODS OF THEIR MANUFACTURING

CROSS-REFERENCE TO RELATED APPLICATIONS

This application claims priority to Swedish Application No. 2251130-7, filed Sep. 30, 2022, which is hereby incorporated by reference in its entirety.

TECHNICAL FIELD

The present invention relates generally to improvements in preparing therapeutically active limonoids as well as new limonoid-type compounds.

BACKGROUND

EP 2807170 discloses limonoids derived from plants useful for treatment of sexual dysfunction and having a sexually enhancing effect. It is suggested herein to use phragmalin esters extracted from the source of seeds of *Chukrasia tabularis* and with lengthy processes including alkaline hydrolysis, conversion to a Weinreb amide and by relocation of the phragmalin lactone ring obtain the desired limonoids. As a result, the production processes in EP 2807170 give a low yield and the raw material from *Chukrasia tabularis* is difficult to access, it will be an excessively difficult and expensive way of producing the limonoids in reasonable quantities to develop and launch a limonoid based therapeutic product. It is therefore a need for more effective ways of producing the desirable limonoids.

SUMMARY

The present document is directed to a method of obtaining at least one of the compounds of Formula Ia and Formula Ib:

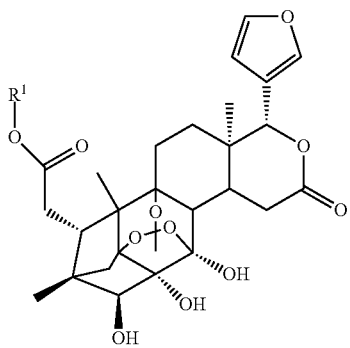

Formula Ia

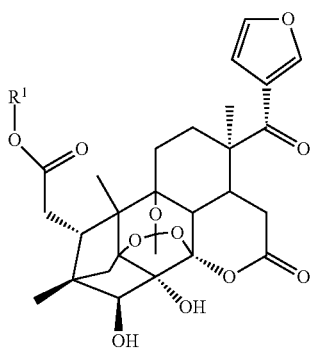

Formula Ib wherein R1 is a straight, branched or cyclic alkyl group with 1 to 6 carbon atoms that is unsubstituted or substituted with e.g. OH or a halogen, such as F, said method comprising:
(i) providing a composition comprising:
at least one of the compounds of Formula IIa and Formula IIb,

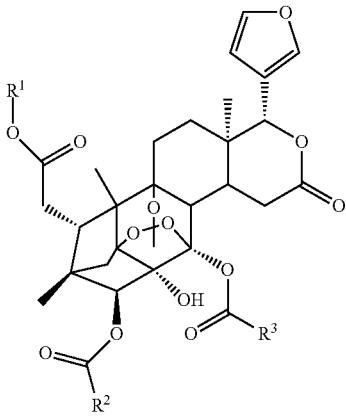

Formula IIa

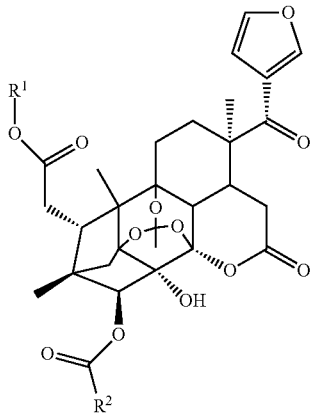

Formula IIb wherein
R1 is as defined above,
R2 and R3 independently are selected from straight, branched or cyclic, substituted or unsubstituted alkyl groups with 1 to 6 carbons or from a nicotinyl group;
and/or providing an extract composition from *Entandrophragma caudatum*, comprising at least the compound of Formula IIa, wherein
a) R2 and R3 independently are selected from straight or branched alkyl groups with 1 to 6 carbon atoms or a nicotinyl group; and
b) R1 is methyl;
(ii) subjecting the extract composition and/or optionally the composition from step (i) to one or more distillations and to an introduction of a solvent comprising an aliphatic alkanol;
(iii) performing an alkanolysis reaction by, in the presence of the aliphatic alcohol, adding an aliphatic metal alkoxide to start the reaction, and subsequently an acid, preferably an organic acid, such as acetic acid, to stop the alkanolysis reaction, thereby obtaining at least one of the compounds of Formula Ia and Formula Ib.

The present document also discloses a method of producing compounds of Formula Ib from compounds of Formula Ia comprising:

(i) reacting a compound of Formula Ia with a base, of sufficient strength to open the lactone ring, but not to hydrolyze the group R1 to form a carboxylic group, preferably the base is barium hydroxide octahydrate in methanol, to obtain a compound of Formula III;

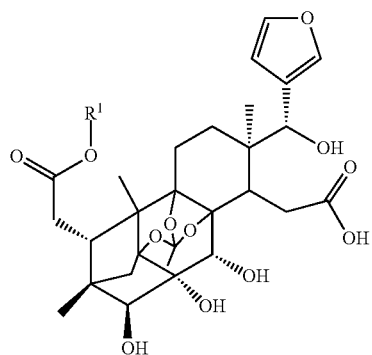

Formula III (ii) reacting a compound of Formula III with a selectively oxidizing agent, preferably Dess Martin periodinane, to obtain a compound of Formula IV; and

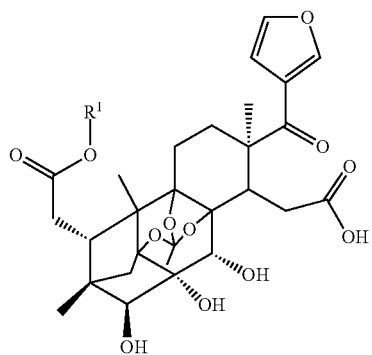

Formula IV (iii) reacting a compound of Formula IV with a coupling agent, preferably a carbodiimide coupling agent, such as 1-(3-dimethylaminopropyl)-3-ethylcarbodiimide hydrochloride (EDC·HCl) in the presence of a sterically hindered organic base, preferably N,N-diisopropylethylamine (DIPEA), thereby obtaining a compound of Formula Ib.

The present document is also directed to a method for producing a compound of Formula V from a compound of Formula Ib by reacting a compound of Formula Ib with an esterification agent and a sterically hindered base to selectively introduce the group R2' of Formula V,

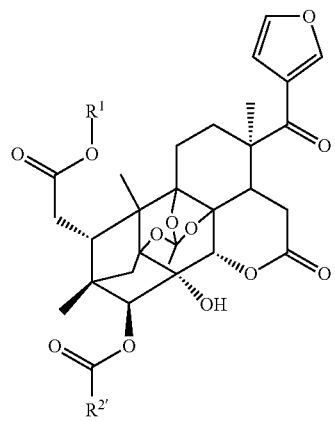

Formula V wherein R2' is a straight, branched or cyclic optionally substituted alkyl group with 1 to 6 carbon atoms.

The present document is also directed to a compound of Formula III. (The present document is also directed to a compound, wherein R1 is methyl.

The present document is also directed to a compound, obtained or obtainable by the method of step (i).

The present document is also directed to a compound of Formula IV. The present document is also directed to a compound wherein R1 is methyl.

The present document is also directed to a compound obtained or obtainable by the method of step (ii).

The present document is also directed to a monohydrate of compound according to Formula V, wherein R1 preferably is methyl.

The present document is also directed to a compound according to Formula V with the proviso that R1 is not hydrogen, methyl or ethyl.

The present document is also directed to an extract composition of *Entandrophragma caudatum* prepared from seeds of *Entandrophragma caudatum*, said extract composition of *Entandrophragma caudatum* comprising at least one of a compound according to Formula IIa and Formula IIb wherein the extract composition of *Entandrophragma caudatum* is produced by:

(i) mixing ground seeds of *Entandrophragma caudatum* with methanol, filtering, collecting and concentrating to obtain a concentrated methanol extract;

(ii) mixing the concentrated methanol extract with a less polar solvent and a more polar solvent to obtain a two-phase composition and discarding the more polar solvent phase to eliminate polar impurities and concentrating the less polar solvent phase, preferably by distillation, thereby obtaining the extract composition of *Entandrophragma caudatum*.

"Less polar" and "more polar" solvent in this method refers to the polarity of the solvents in relation to each other.

The present document is also directed to a method for producing an extract composition of *Entandrophragma caudatum* prepared from seeds of *Entandrophragma caudatum*, said extract composition of *Entandrophragma caudatum* comprising at least one of a compound according to Formula IIa and/or a precursor to Formula Ib, said method comprising the steps of:

i) mixing ground seeds with methanol, filtering, collecting and concentrating to obtain a concentrated methanol extract;

ii) mixing the concentrated methanol extract with a less polar solvent and a more polar solvent to obtain a two-phase composition and discarding the more polar solvent phase to eliminate polar impurities and concentrating the less polar solvent phase, preferably by distillation, thereby obtaining the extract composition of *Entandrophragma caudatum*.

"Less polar" and "more polar" solvent in this method refers to the polarity of the solvents in relation to each other.

The present document is also directed to a method of producing the monohydrate of Formula VI

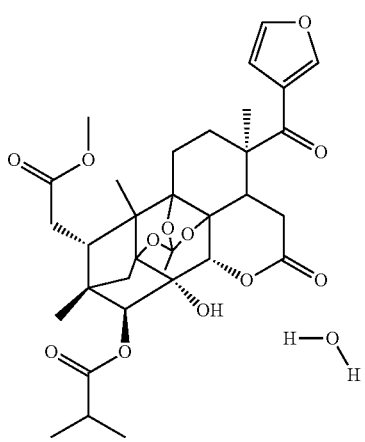

Formula VI said method comprising the steps of:
(i) employing the method to obtain at least of a compound of Formula Ia, wherein R1 is methyl and a compound of Formula Ib wherein R1 is methyl;
(ii) separately collecting and converting a compound of Formula Ia to a compound according to Formula Ib with the method; and
(iii) employing a method to convert a compound according to Formula Ib, collected from steps (i) and (ii), to obtain a compound of Formula IIb wherein R2 is isopropyl.

DETAILED DESCRIPTION

Figure 1A:
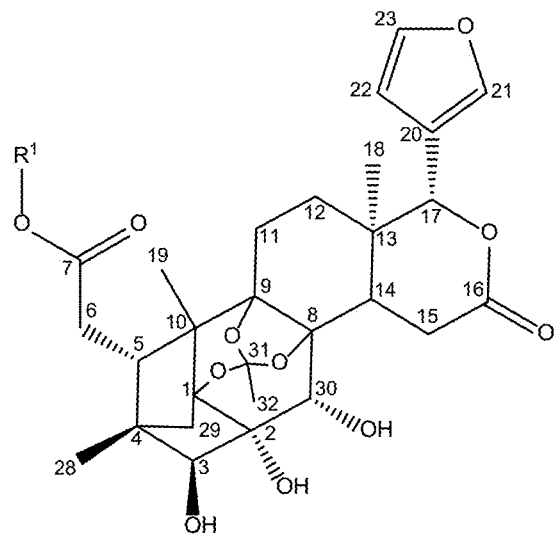
FIG. 1 shows the numbering of the carbon atoms of a compound of Formula Ia (FIG. 1 *a*) and Formula Ib (FIG. 1*b*), respectively.
Figure 1B:
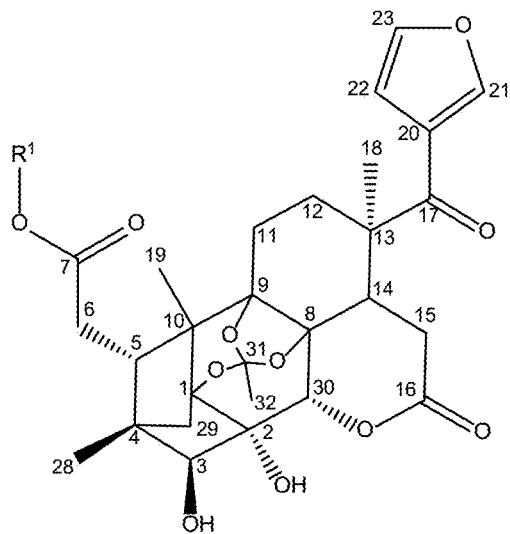

Method for Obtaining a Compound of Formula Ia and/or Formula Ib

The present document is directed to methods enabling an increased yield to e.g. enable upscaling and industrial commercial production of therapeutically active limonoids as well as new limonoid-type compounds to be obtained.

In one aspect, the invention relates to a method of obtaining the compounds according to Formula Ia and Formula Ib

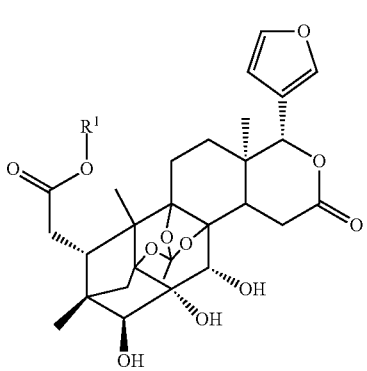

Formula Ia

Formula Ib wherein R1 is a straight, branched or cyclic alkyl group with 1 to 6 carbon atoms that is unsubstituted or substituted with one or more groups selected from OH and halogen. For example, R1 can be a methyl or a trifluoromethyl group.

The method includes providing a composition comprising at least one of the compounds of Formula IIa and Formula IIb:

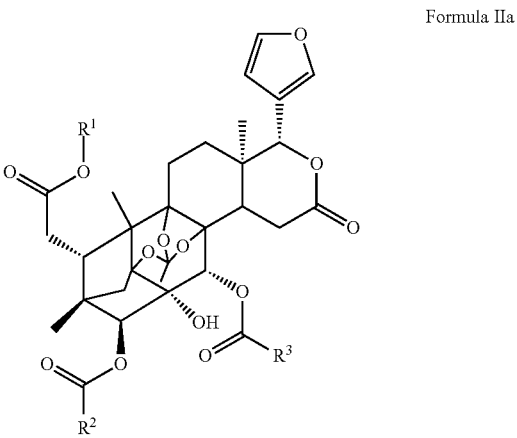

Formula IIa

-continued

Formula IIb

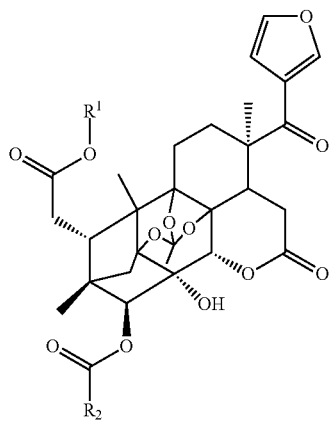

wherein R1 is as defined above, and R2 and R3 independently are selected from straight, branched or cyclic, substituted or unsubstituted alkyl groups with 1 to 6 carbons or from a nicotinyl group.

In the composition the compounds of Formula IIa and/or IIb can be of natural or synthetic origin and the composition may comprise at least one alkanol solvent suitable for the following alkanolysis step. Alternatively in the method or as a complement to the mentioned composition, an extract composition of *Entandrophragma caudatum* is provided (see below). The extract composition of *Entandrophragma caudatum* comprises at least a compound of Formula IIa, wherein R2 and R3 independently are selected from straight or branched alkyl groups with 1 to 6 carbon atoms or a nicotinyl group; and R1 is methyl. As a next step of the method, the mentioned composition comprising at least one of the compounds of Formula IIa and Formula IIb and/or the mentioned extract composition of *Entandrophragma caudatum* is/are optionally subjected to one or more distillations for the purpose of removing water and any other solvent may disturb the following alkanolysis. In this step an alkanol solvent is introduced that complies with the following alkanolysis. The alkanol preferably is selected from straight or branched C1-C6 alcohols.

The alkanolysis is performed by adding an aliphatic metal alkoxide to start the reaction, and subsequently an acid, preferably an organic acid, such as acetic acid, to stop the reaction, thereby obtaining at least one of the compounds of Formula Ia and Formula Ib.

In embodiments, the method is performed with the extract composition of *Entandrophragma caudatum*.

The extract composition of *Entandrophragma caudatum* preferably comprises at least one of phragmalin-3,30-di-isobutyrate, phragmalin-3-isobutyrate-30-proprionate, phragmalin-3-nicotinate-30-isobutyrate and/or at least one precursor to the compound of Formula Ib.

The following purification process of purifying the mixture of at least one of the compounds of Formula Ia and Formula Ib obtained from the alkanolysis, generally comprises, consecutive extractions with polar and non-polar fluids to remove polar and non-polar impurities. The purification process comprises steps of drying the mixture, for example with water absorbents, to remove water and using polar extraction fluids and steps of concentration under reduced pressure. In embodiments of the purification process, polar impurities may first be removed with one or several polar fluids before drying and concentrating before removing non-polar impurities with one or more non-polar/non-water miscible fluids.

In embodiments of the method, the step of removing polar impurities from the compounds of Formula Ia and Formula Ib, may comprise removing the solvent comprising an alkanol of the alkanolysis; adding one or more polar extraction fluids, and optionally removing water by adding a water absorbing agent e.g. selected from of sodium sulphate, $MgSO_4$, $CaSO_4$, $CaCl_2$) $K2CO_3$ to obtain a crude mixture of said compounds. The polar extraction fluids can be ethyl acetate, water, or mixtures thereof, an aqueous sodium chloride solution. However, a skilled person can find similarly useful alternatives.

In embodiments of the method, the step of removing non-polar impurities by dissolving said non-polar impurities in a non-polar/non-water miscible solvent, preferably hexane or a solvent with polarity index similar to hexane, such as pentane, cyclohexane, heptane and discarding the solvent phase with said nonpolar impurities to obtain a crude mixture.

In embodiments of the method, it comprises concentrating the crude mixture obtained or obtainable according to the above by removing polar impurities as outlined above and contacting it at least once with the non-polar/non-water miscible solvent according as previously outlined, thereby obtaining compounds of Formula Ia and/or Formula Ib in solid form.

In embodiments of the method, it comprises a step of chromatographically separating compounds of Formula Ia from compounds of Formula Ib and individually collecting and purifying compounds of Formula Ia and Formula Ib, respectively. Preferably a final purity of each of the compounds is at least 90%. Preferably the chromatography is performed after the consecutive steps of removing polar and non-polar impurities.

In embodiments of the method, the alkanolysis is a methanolysis reaction in a methanol solvent, comprising adding a methoxide, preferably sodium methoxide Method for Producing a Compound of Formula Ib In one aspect, the present invention relates to a method of producing compounds of Formula Ib from compounds of Formula Ia (comprising as a first step reacting a compound of Formula Ia with a base, of sufficient strength to open the lactone ring, but not to hydrolyze the group R1 to form a carboxylic group, preferably the base is barium hydroxide octahydrate in methanol, to obtain a compound of Formula III. For the lactone ring opening, the skilled person can find alternatively suitable bases, comprising hydroxy groups or alternatively by an acid, enzymatically, or for example with sodium trimethylsilanolate ((TMS)ONa).

Formula III

[chemical structure]

In a second step the method comprises reacting a compound of Formula III with a selectively oxidizing agent to obtain a compound of Formula IV.

Formula IV

[chemical structure]

The oxidizing agent in the second step is selected from Dess Martin periodinane, pyridinium chlorochromate, Swern oxidation (oxalyl chloride and DMSO), Corey-Kim oxidation, Jones oxidation (Chromium trioxide), TEMPO, and Burgess reagents. Preferably, the oxidizing agent is Dess Martin periodinane.

In a third step, the method comprises reacting a compound of Formula IV with a coupling agent, in the presence of a sterically hindered organic base, thereby obtaining a compound of Formula Ib with a displaced lactone ring.

The coupling agent in the third step is selected from carbodiimide coupling agents, such as 1-(3-dimethylamino-propyl)-3-ethylcarbodiimide hydrochloride (EDC·HCl), N,N'-dicyclehexylcarbodiimide (DCC), N,N'-diisopropyl-carbodiimide (DIC), and DCC/HOBt (hydroxybenzotri-alzole). Preferably, the coupling agent is 1-(3-dimethylami-nopropyl)-3-ethylcarbodiimide hydrochloride.

The sterically hindered organic base in the coupling reaction of the third step is selected from N-diisopropyleth-ylamine (DIPEA), Dimethyl-aminopyridine (DMAP),Tri-ethylamine (TEA), and 4-pyrrolidino pyridine (PPY), Preferably, the base is preferably N,N-diisopropylethylamine (DIPEA).

Method for Producing a Compound of Formula V

In one aspect, the invention relates to a method for producing a compound of Formula V from a compound of Formula Ib by reacting a compound of Formula Ib with an esterification agent and a sterically hindered base to selectively introduce the group R2' in Formula V.

Formula V

[chemical structure]

In Formula V, R2' is a straight, branched or cyclic optionally substituted alkyl group with 1 to 6 carbon atoms and R1 is as previously defined. The skilled person can conceive a number of different esterification agents such acid chlorides, anhydrides and the similar. Useful sterically hindered bases are mentioned in the previous section. Preparation of a compound according to Formula Ib is performed according to what is outlined in previous sections.

In one embodiment of the method to produce compounds of Formula V, R2' is isopropyl and R1 is methyl, the esterification agent is isobutyryl chloride, and wherein DMAP-HCl is used as the sterically hindered base.

In embodiments, the method of producing compounds of Formula V, can further comprise consecutively purifying the compound of Formula V with a polar solvent and a polar solvent, and finally washing said compound with a dual polarity solvent, preferably acetone and water, thereby obtaining a solid monohydrate of a compound of Formula V.

Compounds

In one aspect, the invention relates to a compound of Formula III. In embodiments, the compound has methyl as substituent R1. In embodiments, the Formula III obtained or obtainable by the method as previously outlined.

In one aspect, the invention relates to a compound of Formula IV. In embodiments, the compound has methyl as substituent R1 and is obtained or obtainable by the method as previously outlined.

In one aspect, the invention relates to the monohydrate of compound according to Formula V, such as a compound having methyl as the substituent preferably R1.

In one aspect, the invention relates to compound according to Formula V with the proviso that R1 is not methyl, ethyl or hydrogen.

Extract Composition of *Entandrophragma caudatum* and Methods for its Production In another aspect of the invention, it relates to an extract composition of *Entandrophragma caudatum* prepared from seeds of *Entandrophragma caudatum*, The extract composition of *Entandrophragma caudatum* comprises at least one of a compound according to Formula IIa and Formula IIb and/or precursor to a compound of Formula Ib.

The extract composition of *Entandrophragma caudatum* is a natural product extracted from ground seeds of *Entandrophragma caudatum*. The seeds are charged to a glass reactor and methanol is added for the extraction. The slurry is mixed for at least 15 h at 40° C. followed by a filtration under inert N2-gas pressure. Additional methanol is added to wash the filter cake and piping. The filtered solution containing the extracted material is led to a vessel and charged back in portions to the glass reactor for concentration through vacuum distillation and a methanol extract is obtained. The methanol extract is concentrated to dryness, dissolved in ethyl acetate and washed with water. The ethyl acetate is concentrated and the extract composition of *Entandrophragma caudatum* is collected as a dark yellow solution in ethyl acetate. The extract composition of *Entandrophragma caudatum* comprises phragmalin-3,30-di-isobutyrate, phragmalin-3-isobutyrate-30-proprionate, phragmalin-3-nicotinate-30-isobutyrate and a precursor to the compound of Formula Ib.

For example, the extract composition of *Entandrophragma caudatum* may be produced by:
i) mixing ground seeds of *Entandrophragma caudatum* with methanol, filtering, collecting and concentrating to obtain a concentrated methanol extract;
ii) mixing the concentrated methanol extract with a less polar solvent and a more polar solvent to obtain a two-phase composition and discarding the more polar solvent phase to eliminate polar impurities and concentrating the less polar solvent phase, preferably by distillation, thereby obtaining the extract composition of *Entandrophragma caudatum*.

In embodiments of the extract composition, the less polar solvent in step forms an azeotrope with the more polar solvent. Preferably the less polar solvent is ethyl acetate and the more polar solvent is water, but other combinations less polar/more polar solvents are conceivable for a skilled person. More preferably, the less polar solvent and more polar solvent is ethyl acetate and water, respectively, in a volume ratio of 2:1.

In embodiments of the extract composition, it comprises at least one of the compounds phragmalin-3,30-di-isobutyrate and phragmalin-3-isobutyrate-30-proprionate, phragmalin-3-nicotinate-30-isobutyrate and a precursor to the compound of Formula Ib.

In another aspect of the invention, it relates to a method for producing an extract composition of *Entandrophragma caudatum*, as above, prepared from seeds of *Entandrophragma caudatum*, said extract composition of *Entandrophragma caudatum* comprising at least one of a compound according to Formula IIa and Formula IIb said method comprising the steps of:
i) mixing ground seeds of *Entandrophragma caudatum* with methanol, filtering, collecting and concentrating to obtain a concentrated methanol extract;
ii) mixing the concentrated methanol extract with a less polar solvent and a more polar solvent to obtain a two-phase composition and discarding the more polar solvent phase to eliminate polar impurities and concentrating the less polar solvent phase, preferably by distillation, thereby obtaining the extract composition of *Entandrophragma caudatum*.

In embodiments of the method, the less polar solvent in step ii) forms an azeotrope with water, preferably the less polar solvent comprises ethyl acetate and the more polar solvent comprises water. Preferably, the less polar solvent and more polar solvent in step ii) is ethyl acetate and water, respectively, more preferably in a volume ratio of 2:1.

Method for Producing a Monohydrate of a Compound of Formula VI

In yet another aspect of the invention, it relates to a method of producing the monohydrate of Formula VI.

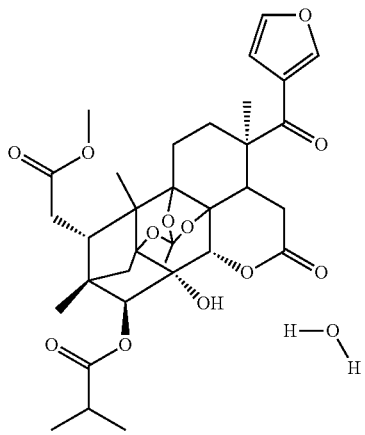

Formula VI

The method comprises the steps of employing the previously outlined methods to obtain of at least of a compound of Formula Ia, wherein R1 is methyl and/or a compound of Formula Ib, wherein R1I is methyl. As a next optional step, a compound of Formula Ia is separately collected and converted to a compound according to Formula Ib with the previously outlined methods. A previously outlined method is then used to convert collected compound according to Formula Ib, wherein R2 is isopropyl, see Formula VI. Finally, a purification and washing method as earlier outlined is applied to obtain a monohydrate of Formula VI.

In embodiments of the method, the starting material is an extract composition of *Entandrophragma caudatum*, prepared as described above.

Experimental Section

Example 1: Preparation of Extract Composition from Seeds of *Entandrophragma caudatum*

Overview of the Procedure:

The extract composition of *Entandrophragma caudatum* is a natural product extracted from ground seeds of *Entandrophragma caudatum*. The seeds are charged to a glass reactor and methanol is added for the extraction. The slurry is mixed for at least 15 h at 40° C. followed by a filtration under inert N2-gas pressure. Additional methanol is added to wash the filter cake and piping. The filtered solution containing the extracted material is led to a vessel and charged back in portions to the glass reactor for concentration through vacuum distillation and a methanol extract is obtained. The methanol extract is concentrated to dryness, dissolved in ethyl acetate and washed with water. The ethyl acetate is concentrated and the extract composition of *Entandrophragma caudatum* is collected as a dark yellow solution in ethyl acetate. The extract composition of *Entandrophragma caudatum* comprises phragmalin-3,30-di-isobutyrate, phragmalin-3-isobutyrate-30-proprionate, phragmalin-3-nicotinate-30-isobutyrate and a precursor to the compound of Formula Ib.

Figure 2:
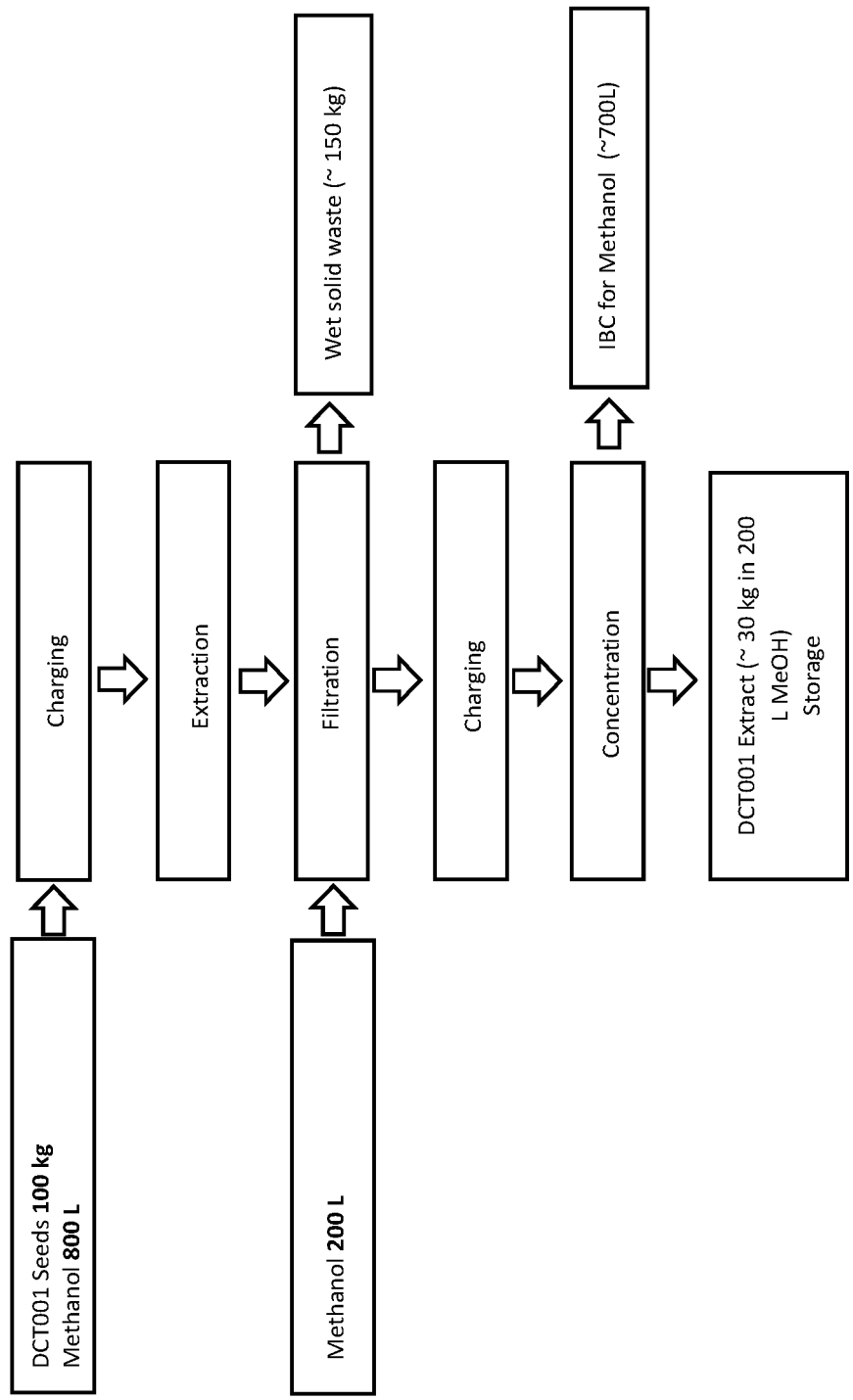
FIG. 2 shows an overview of the preparation of a methanol extract of seeds from *Entandrophragma caudatum*.

Detailed Description of the Procedure:

Step 1: Preparation of a Methanol Extract (See FIG. 2 for an Overview of the Procedure)

Methanol (ca 800 L) was charged to a nitrogen filled glass reactor and stirring started. Ca 100 kg of ground seeds of

*Entandrophragma caudatum* was added. The glass reactor was then evacuated and refilled with nitrogen. The temperature of the reactor was set to 40° C. and the contents stirred for at least 15-20 hours. The mixture was then filtered on a polyamide filter cloth (25 μm) by applying pressurized nitrogen atmosphere and the filtrate was collected in a vessel. Methanol was then charged to the feeding vessel (ca 100 L) and methanol was charged from the feeding vessel directly to the filter bypassing the glass reactor (twice, 50 L per time) and the filtrate collected into a vessel. The mixture was then again filtered on the polyamide filter cloth by repeating the procedure. The filter cake was then dried under vacuum for at least an hour. The filtrate was then charged into the glass reactor (ca 800 L in total) and the contents stirred. The methanol solvent was then distilled off under vacuum at a temperature of 40-70° C. jacket temperature (internal temperature during distillation was approx. 21-29° C.). The distillation was continued until approx. 200 L was left in the glass vessel. Care has to be taken to not distill too much of the methanol off as the remaining content will be too sticky to be removed from the glass vessel. The jacket temperature was then adjusted to approx. 20-25° C. and the concentrated methanol extract was collected.

Figure 3:
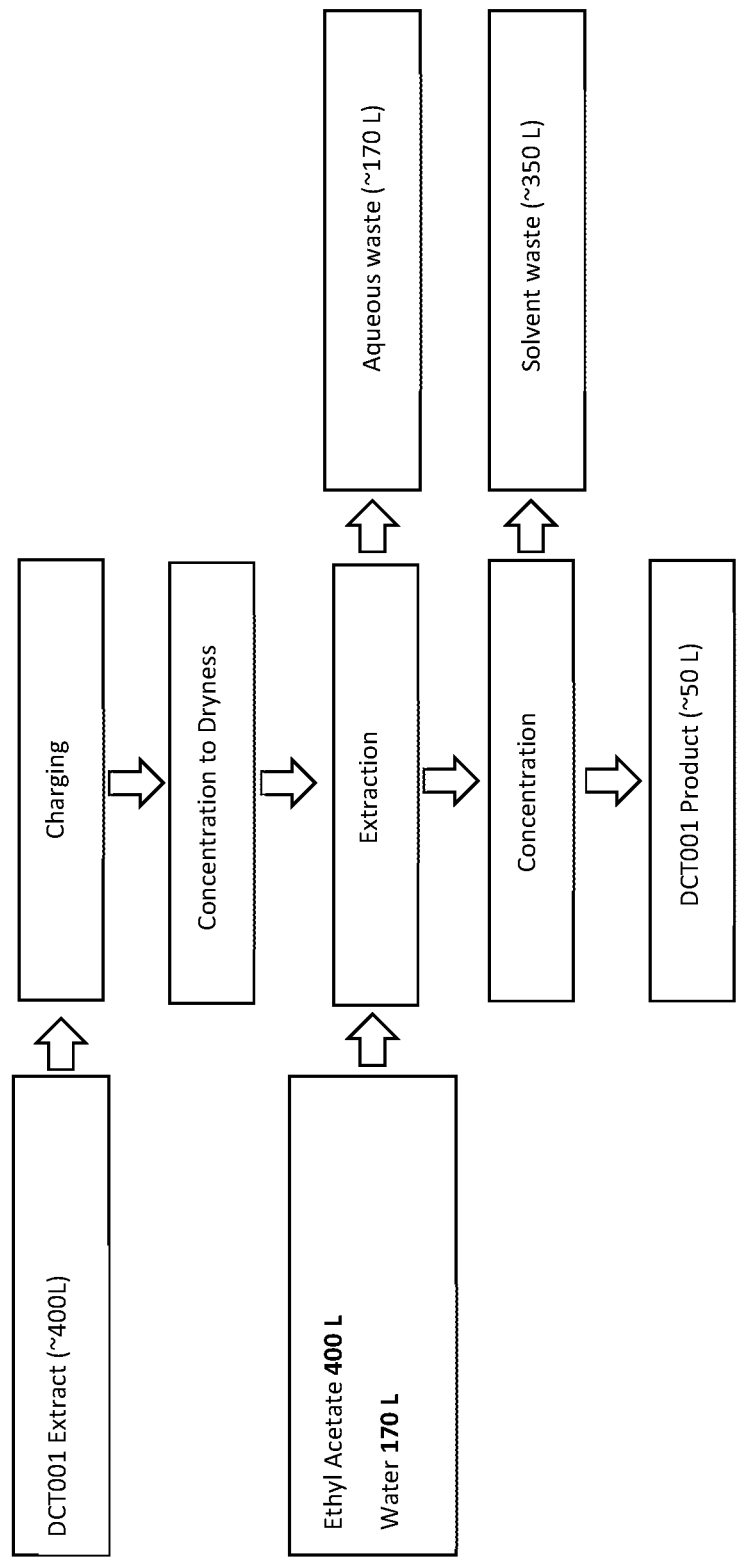
FIG. 3 shows an overview of the preparation of an extract composition of *Entandrophragma caudatum* in ethyl acetate.

Step 2: Preparation of the Extract Composition of *Entandrophragma caudatum* in Ethyl Acetate (See FIG. 3 for an Overview of the Procedure)

Concentrated methanol extract as prepared in step 1 above (ca 400 L, i.e. two batches of step 1) were charged to a nitrogen filled glass reactor and the temperature of the reactor adjusted to 75° C. and the stirrer started.

The methanol was distilled off under vacuum to obtain a dry mixture and the temperature thereafter adjusted to 20° C.

Ethyl acetate (EtOAc) (ca 400 L) was then charged into the reactor. Thereafter water (ca 170 L) was charged. The temperature of the reactor was set to 40° C. and the contents of the reactor stirred for ca 30 min while maintaining the temperature at 40° C.

The stirrer was then stopped and the two phases were allowed to separate for 30 to 60 min, until layer separation was achieved. The aqueous layer was then discarded.

The temperature of the reactor was then adjusted to 55-75° C. and the mixture remaining after water removal was concentrated under vacuum. The distillation was stopped when the volume had been reduced to ca 50 L (i.e. when ca 350 L of distillate had been collected). The extract composition of *Entandrophragma caudatum* in ethyl acetate was then collected. When stored before further use, the extract composition was stored at 5° C.±3° C.

Example 2—Synthesis of Compounds of Formula V

Figure 4:
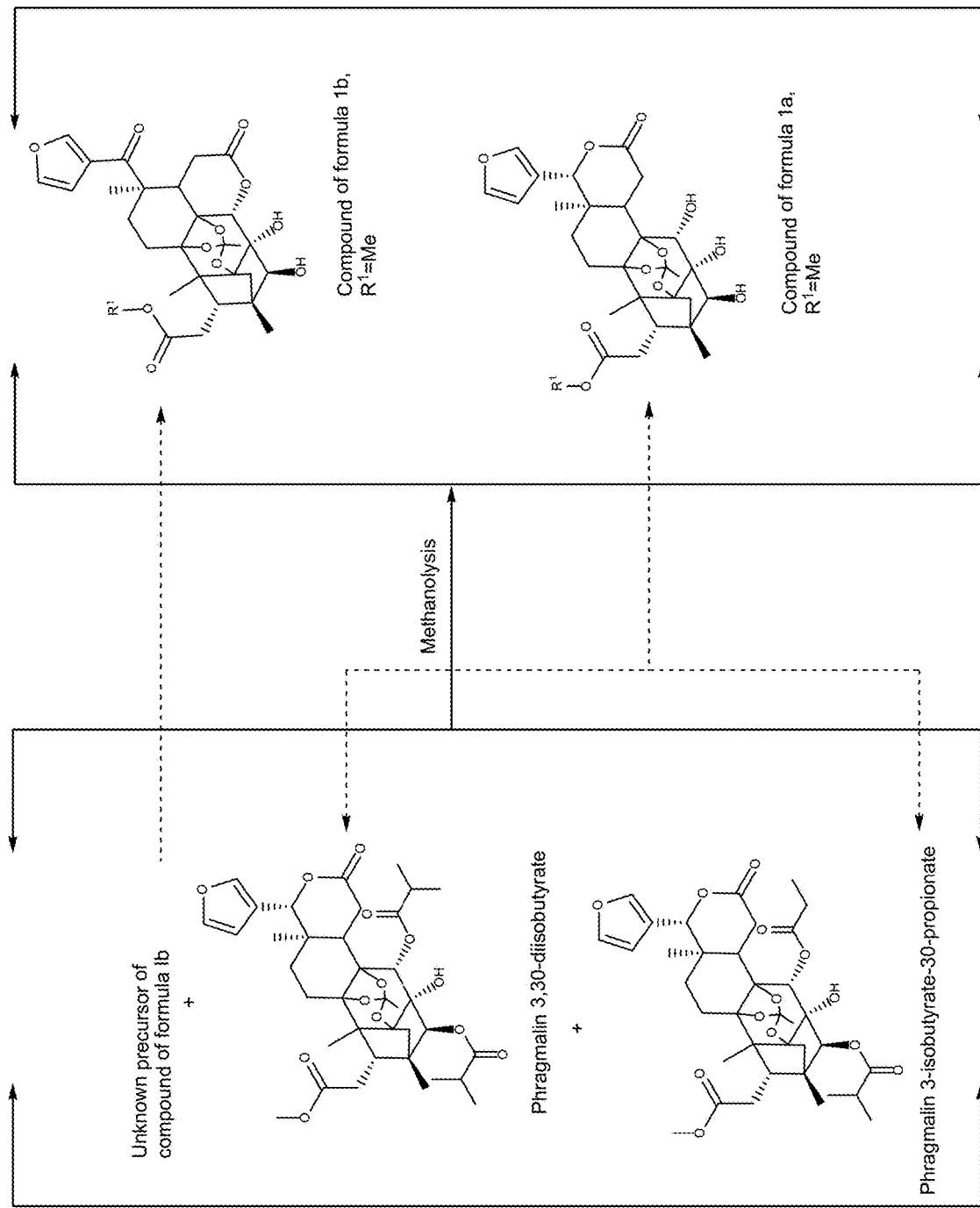
FIG. 4 shows an overview of the methanolysis reaction performed according to Example 2.

Overview of the Procedure (Also See FIG. 4)

The starting material for the synthesis of compounds of formula V contains a mixture of extracted material from seeds of *Entandrophragma caudatum*, and remaining solvents from the extraction procedure. This extract composition of *Entandrophragma caudatum* was prepared according to Example 1.

The starting material contains about 10% of primarily two different compounds of Formula IIa molecules and probably one or more precursor molecules to compounds of Formula Ib, as materials of interest for further synthesis.

The two most important molecules of Formula IIa identified in the extract composition of *Entandrophragma caudatum* are:
a. Phragmalin 3,30-diisobutyrate
b. Phragmalin 3-isobutyrate-30-propionate The precursor molecules of formula Ib are not fully identified.

The two compounds of Formula IIa and the probable precursor of Formula Ib in the seed extract are converted to compound of Formula Ia and Ib respectively through the methanolysis procedure followed by purification to give pure compounds of Formula Ia and Ib. The compound of Formula Ia is then converted to the compound of Formula Ib in three synthetic steps. Compound of Formula Ib is finally converted to a compound of Formula V in one step.

Detailed Description of Procedure

Transformation of the compounds of formula IIa and precursor to formula Ib to a compound of Formula Ia and Ib Methanolysis:

An overview of the methanolysis reaction is depictured in FIG. 4.

The ethyl acetate extract (138 Kg from previous steps)) was dissolved in methanol (690 L, 5 vol) and distilled until no distillate was observed. Methanol (690 L,5 vol) was added to mass and further distilled until no distillate was observed at 45° C. to afford 105 kg of solvent free extract residual as a brown syrup.

The extract residual (105 kg, 1.0 eq) was dissolved in methanol (1050 L, 10.0 V) and cooled to 15±5° C. Sodium methoxide (15.75 kg, 0.15% w/w) was added in four equal lots with a time interval of 10 minutes between each addition at temperature below 30° C. (exotherm of 5-10° C. is observed during addition of sodium methoxide). Reaction mixture was stirred for 40 h at 45±5° C.

Workup:

pH of reaction mass was adjusted to 6.0 to 7.0 using acetic acid (~15.75 kg, ~0.15% w/w) at 15±5° C. and purified water (315 L, 3.0 V) was added below 30° C. Reaction mass was concentrated under reduced pressure at temperature less than 45° C. to remove methanol. Residue was diluted with ethyl acetate (1050 L, 10.0 V), added purified water (420 L, 4.0 V) followed by sodium chloride (21 kg, 0.2% w/w) and stirred for 15 min. Biphasic medium was separated and re-extracted with ethyl acetate (735 L, 7.0 V). Combined organic layer was washed with 10% sodium chloride solution (735 L, 7.0 V), separated, and dried over anhydrous sodium sulfate (~21 kg, 0.2% w/w). Organic layer was concentrated under reduced pressure at temperature less than 45° C. to afford crude mixture of compound of formula Ia and Ib.

Hexane Slurry Followed by Column Purification:

Hexane (1050 L, 10.0 V) was added into the residue, heated to 40±5° C. and stirred for 2 hours. Mixture was cooled to 25±5° C. and stirred for 8 hours. Precipitated solids were collected by filtration and washed with hexane (210 L, 2.0 V) to afford about 13.36 kg crude mixture of compounds of formula Ia and Ib as a pale yellow solid (All non-polar impurities were washed out with hexan purification). The compounds of formula Ia and Ib were separated from crude mixture by column chromatography. About 4.17 kg of compound of formula Ia and 2.94 kg of a compound of formula Ib were obtained after column chromatography.

Purification of a Compound of Formula Ia:

Crude compound of formula Ia (4.17 kg) was stirred with isopropyl alcohol (IPA) (8.3 L, 2.0 V) at 50±5° C. for 1 hour and slowly allowed to 25±5° C., stir for 6 hours. Solids were collected by filtration and washed with IPA (2.1 L, 0.5 V). Wet solid (2.32 kg) was dried under vacuum tray drier at 40±5° C. to get about 2.13 kg of compound of formula Ia.

Analytical data: Purity (HPLC): 98.4%

Purification of Compound of Formula Ib:

Crude compound of formula Ib (2.94 kg) was stirred with IPA (8.8 L, 3.0 V) at 50±5° C. for 1 hour and slowly allowed to 25±5° C., stir for 6 hours. Solids were collected by filtration and washed with IPA (2.9 L, 1.0 V).

Wet solid (1.53 kg (after LOD correction)) was stirred with ethyl acetate (4.6 L, 3.0 V) at 50±5° C. for 1 hour and slowly allowed to 25±5° C., stir for 6 hours. Solids were collected by filtration and washed with ethyl acetate (1.5 L, 1.0 V).

Wet solid (1.07 kg) was stirred with ethyl acetate (4.6 L, 3.0 V) at 50±5° C. for 1 hour and slowly allowed to 25±5° C., stir for 6 hours. Solids were collected by filtration and washed with ethyl acetate (1.5 L, 1.0 V).

Wet solid (0.85 kg) was stirred with ethyl acetate (1.7 L, 2.0 V) at 50±5° C. for 1 hour and slowly allowed to 25±5° C., stir for 6 hours. Solids were collected by filtration and washed with ethyl acetate (0.4 L, 0.5 V). Wet solid (0.58 kg) was dried under vacuum tray drier at 40±5° C. to get about 0.335 kg of compound of formula Ib.

Analytical data: Purity (HPLC): 99.5%

Figure 5:
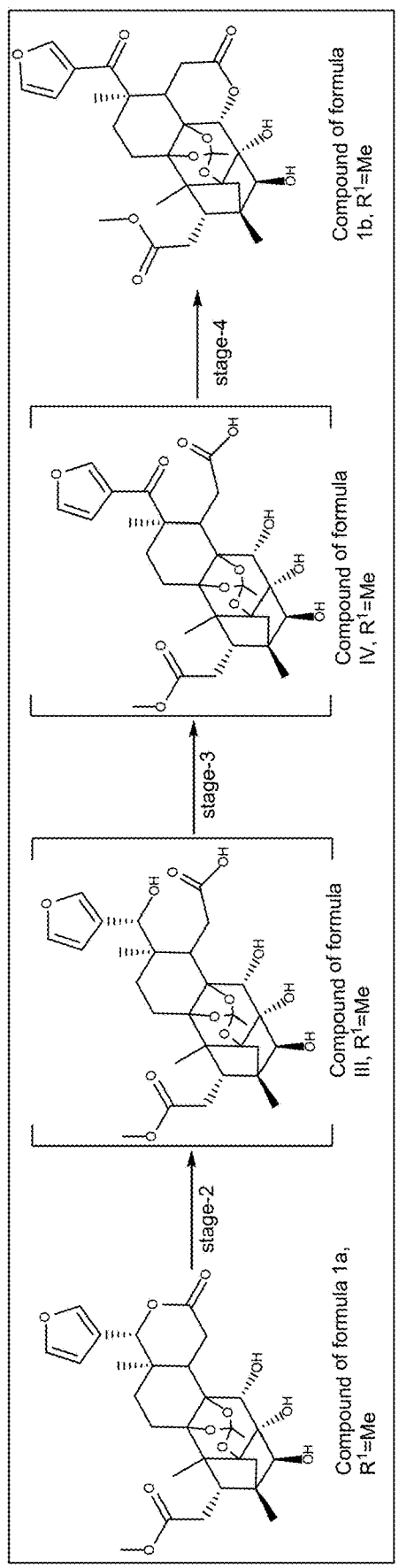
FIG. 5 shows a three-step synthesis for the conversion of compound of Formula Ia to a compound of Formula Ib.

Three step synthesis for the conversion of compound of Formula Ia to a compound of Formula Ib, see FIG. 5.

Step 1: Ring Opening of Lactone Ring (Compound of Formula III)

A suspension of barium hydroxide octahydrate (1.16 kg, 1.0 eq) in methanol (10.3 L, 5.0 V) was cooled to 0-5° C. and a compound of formula Ia (2.06 kg, 1.0 eq) was added in 4 equal lots over a period of 15 min at 0-5° C. The resulting reaction mixture was stirred at 0-10° C. for 2 h (reaction mass turns homogenous as the reaction progresses). The progress of reaction was monitored by TLC (60% ethyl acetate/hexane, for starting material consumption and 10% methanol/methylene chloride (MeOH/DCM) for product elution; Visualization: $KMnO_4$ stain).

Workup: After complete consumption of the starting material by TLC, reaction mixture was acidified to pH 5-6 by using 10% aq. acetic acid (~8.24 L, 4.0 V) and concentrated at temperature below 40° C. to remove methanol. Residue was extracted twice with (10.3 L*2, 5 V*2). Combined organic layer was washed with brine solution (8.2 L, 4.0 V), dried over anhydrous sodium sulphate, filtered and organic layer was taken as such for next stage.

Analytical data: Purity (HPLC): 99.5%

Step 2: Oxidation (Compound of Formula IV)

To a stirred organic layer (compound of formula III) was added a suspension of Dess-Martin periodinane (1.72 kg, 1.1 eq) in DCM (16.5 L, 8 V) at 0-5° C. The resulting reaction mixture (white suspension) was stirred at 10-15° C. for 3 h. The progress of reaction was monitored by TLC (5% MeOH/DCM+a drop of AcOH; Visualization: $KMnO_4$ stain).

Workup: After complete consumption of (compound of Formula III) by TLC, reaction mixture was quenched with 20% sodium thiosulphate solution (20.6 L, 10 V) in purified water and stirred for 30 minutes (reaction mass turns clear and clear separation of organic and aqueous layer is observed). The layers were separated, and aq. layer was extracted with DCM (10.3 L, 5.0 V). Combined organic layer was washed with brine solution (10.3 L, 5.0 V), dried over anhydrous sodium sulphate and filtered. The organic layer was concentrated to 10.0 volume level with regards to the compound of formula Ia at below 40° C. and taken as such for next stage.

Step 3: Ring Formation (Compound of Formula Ib)

To a stirred organic layer of compound of Formula IV was added N-(3-dimethylaminopropyl)-N'-ethylcarbodiimide hydrochloride (EDC·HCl) (0.702 kg, 1.0 eq) followed by diisopropylethylamine (DIPEA) (0.957 L, 1.5 eq) over a period of 30 minutes at 10±5° C. Resulting reaction mixture was stirred at 10±5° C. for 2 h. The progress of reaction was monitored by TLC (10% MeOH/DCM for starting material consumption and 80% ethyl acetate/hexane for product elution; Visualization: $KMnO_4$ stain).

Workup: After complete consumption of the compound of formula IV by TLC, reaction mixture was quenched with water (20.6 L, 10.0 L), layers were separated, and aq. layer was extracted with DCM (10.3 L, 5.0 V). Combined organic layer was washed with brine solution (10.3 L, 5.0 V), dried over anhydrous sodium sulphate and filtered. Combined organic layer was dried over anhydrous sodium sulfate and concentrated under reduced pressure at 40° C. until no distillate observed.

Purification of compound of formula Ib: Crude compound of formula Ib was chased with ethyl acetate (12.3 L, 6.0 V) at below 40° C., concentrated to 3.0 vol level with regards to compound of formula Ib and stirred at 50±5° C. for 1 hour. Reaction mass was gradually cooled to 25±5° C. for 1 hour and stirred at 25±5° C. for 6 hours. Solids were collected by filtration and washed with ethyl acetate (2.1 L, 1.0 V) to get 1.1 kg of wet solids of the compound of formula Ib. Wet solids were dried under vacuum tray dryer at 40±5° C. to get 0.85 kg of the compound of Formula Ib.

Analytical data: Purity (HPLC): 95.4%

TABLE 1

| Residual Solvent | | |
|---|---|---|
| Methanol | NMT 3000 ppm | BDL |
| Acetonitrile | NMT 410 ppm | BDL |
| Acetone | NMT 5000 ppm | BDL |
| Dichloromethane | NMT 2000 ppm | 2443 |
| Hexanes | NMT 290 ppm | BDL |
| Ethyl acetate | NMT 10000 ppm | 4198 |
| n-heptane | NMT 5000 ppm | BDL |
| Isopropyl alcohol | NMT 5000 ppm | BDL |

BDL = below detection level,
NMT = not more than

Synthesis of Compound Formula V from Compound of Formula Ib

To a solution of a compound of formula Ib (322 g, 1.0 eq.) in dry dimethyl formamide (DMF) (1.6 L, 5.0 V) was added 4-N,N-dimethylaminopyridine hydrochloride (DMAP·HCl) (91 g) followed by isobutyryl chloride (92 g, 1.5 eq) at 25±5° C. Reaction mass was heated to 60±5° C. and stirred for 6 hours. After 6 hours, to the reaction mass was added DMAP·HCl (45.6 g) followed by isobutyryl chloride (61.2 g, 1.0 eq) at 60±5° C. and the reaction continued for further 4 hours. Reaction was monitored by HPLC.

Workup:

After completion of reaction, reaction mixture was cooled to 25±5° C., filtered through celite bed washed with DMF (320 ml, 1.0 V). Filtrate was passed through 0.2 micron cartridge and washed with DMF (320 ml, 1.0 V).

In another reaction vessel was added purified water (8.0 L, 25.0 V) and cooled to 15±5° C. Filtrate was added slowly to the reaction contents over a period of 1 hour at 15±5° C. (reverse quench). Reaction contents were allowed to attain a temperature of 25±5° C. and stirred for 4 hours at the same temperature. Solids were collected by filtration and washed with purified water (0.65 L, 2.0 V).

Wet solid was stirred with purified water (1.6 L, 5 V) at 40±5° C. for 2 hours. Solids were collected by filtration and washed with purified water (0.65 L, 2 V). Wet solids were dried under reduced pressure at 40±5° C. for 12 hours to afford 456 g of the crude product of formula V (Crude purity by HPLC: 79.97%)

Ethyl Acetate Purification:

Ethyl acetate slurry-1: Crude product (456 g) was stirred with ethyl acetate (1.36 L, 3.0 V) at 50±5° C. for 1 h. Reaction mass gradually allowed to 25±5° C. for 1 hour and stirred at 25±5° C. for 4 h. Solids were collected by filtration, washed with ethyl acetate (0.45 L, 1.0 V). (Wet solid weight: 295 g, after loss of drying (LOD) correction: 249 g (LOD: 15.6% w/w)) (Purity by HPLC: 97.7% and impurities: RRT 0.68: 1.38%)

Ethyl acetate slurry-2: Crude product (249 g) was stirred with ethyl acetate (373 ml, 1.5 V) at 50±5° C. for 1 h. Reaction mass gradually allowed to 25±5° C. for 1 hour and stirred at 25±5° C. for 4 h. Solids were collected by filtration, washed with ethyl acetate (0.45 L, 1.0 V). (Wet solid weight: 236.6 g, after LOD correction: 230 g (LOD: 2.6% w/w)) (Purity by HPLC: 98.68% and impurities: RRT 0.68: 1.38%)

Ethyl acetate slurry-3: Crude product (230 g) was stirred with ethyl acetate (460 ml, 2.0 V) at 50±5° C. for 1 h. Reaction mass gradually allowed to 25±5° C. for 1 hour and stirred at 25±5° C. for 4 h. Solids were collected by filtration, washed with ethyl acetate (115 ml, 1.0 V). (Wet solid weight: 191.6 g, Purity by HPLC: 99.8% and impurities: RRT 0.68: 0.12%)

Wet solids were dried under reduced pressure at 40±5° C. for not less than (NLT) 10 hours to afford 185.4 g of crude compound of formula V.

Acetone/Purified water purification to attain the desired monohydrate form:

Crude compound of formula V (181.4 g) was stirred with acetone (1.3 L, 7.0 V) at 45±5° C. for 30 minutes to get a clear solution. To the reaction mass purified water (2.8 L, 15.0 V) was added over a period of 1 hour and stirred for additional 1 hour at 45±5° C. Gradually cooled the reaction mass to 25±5° C. and stirred for 6 hours. Solids were collected by filtration and washed with acetone/purified water (278 ml, 1.0 V) to afford 188 g of wet product of formula V monohydrate. Wet solids were dried under reduced pressure at 40±5° C. for NLT 16 hours followed by sieving to afford 179 g of compound of formula V monohydrate.

Analytical data: Purity (HPLC): 99.9%

TABLE 2

| Residual Solvent | | |
| --- | --- | --- |
| Solvent | Limit | Result |
| Methanol | NMT 3000 ppm | BDL |
| Acetonitrile | NMT 410 ppm | BDL |

TABLE 2-continued

| Residual Solvent | | |
| --- | --- | --- |
| Solvent | Limit | Result |
| Toluene | NMT 890 | BDL |
| Acetone | NMT 5000 ppm | BDL |
| Dichloromethane | NMT 600 ppm | BDL |
| MTBE | NMT 5000 ppm | BDL |
| Hexane | NMT 290 ppm | BDL |
| Ethyl acetate | NMT 5000 ppm | BDL |
| n-heptane | NMT 5000 ppm | BDL |
| DMF | NMT 880 ppm | BDL |
| Isopropyl alcohol | NMT 5000 ppm | BDL |

BDL = below detection level,
NMT = not more than

Specific optical rotation: −49.8°

Figure 6:
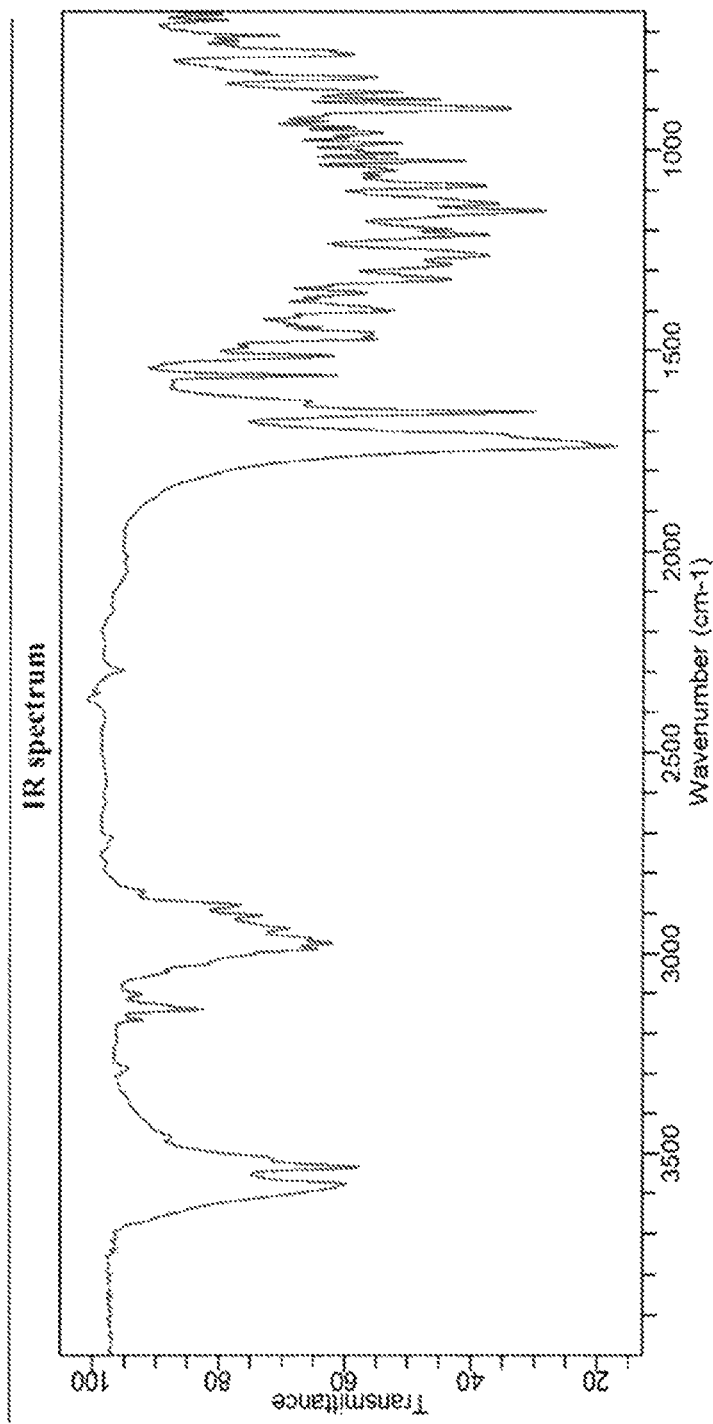
FIG. 6 shows the IR spectrum of a compound of Formula V produced according to Example 2.

The IR spectrum of the compound produced is found in FIG. 6.

NMR data:

$^1$H-NMR (DMSO, 400 MHz): δ 8.64 (s, 1H), 7.78 (s, 1H), 6.75 (dd, 1H), 5.09 (s, 1 H), 4.69 (s, 1H), 3.92 (s, 1H), 3.41 (s, 3H), 2.68 (m, 3H), 2.35 (m, 2H), 2.24 (m, 3 H), 1.95 (m, 2H), 1.67 (m, 1H), 1.55 (d, 4H), 1.42 (s, 3H), 1.26 (d, 6H), 1.18 (m, 1H), 1.04 (s, 1H), 0.76 (s, 3H) LCMS:453.3 [M+H], HPLC purity: 98.50%

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

EP 2807170

The invention claimed is:

1. A compound of Formula III

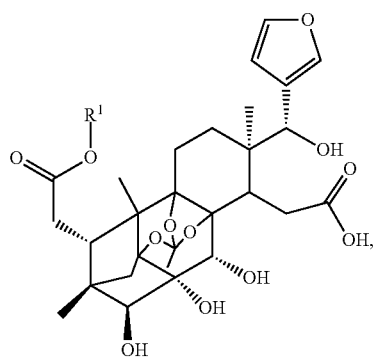

Formula III wherein $R^1$ is a straight branched or cyclic alkyl group with 1 to 6 carbon atoms that is unsubstituted or substituted.

2. The compound according to claim 1, wherein $R^1$ is methyl.

3. The compound according to claim 1, wherein the compound of formula III is obtained by reacting a compound of Formula Ia with a base, of sufficient strength to open the lactone ring, but not to hydrolyze the group R1 to form a carboxylic group, preferably the base is barium hydroxide octahydrate in methanol, to obtain the compound of Formula III

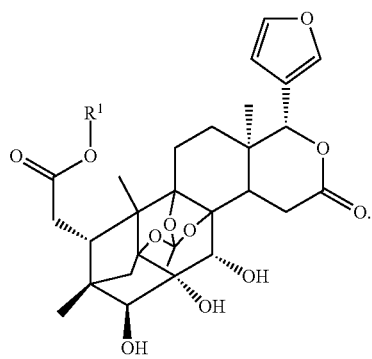

Formula Ia

4. A compound of Formula IV

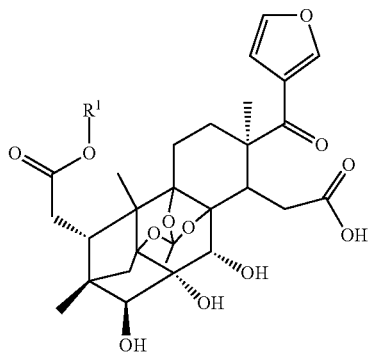

Formula IV wherein $R^1$ is a straight, branched or cyclic alkyl group with 1 to 6 carbon atoms that is unsubstituted or substituted.

5. The compound according to claim 4, wherein $R^1$ is methyl.

6. The compound according to claim 4, wherein the compound of Formula IV is obtained by reacting a compound of Formula III with a selectively oxidizing agent, preferably Dess Martin periodinane, to obtain the compound of Formula IV.

7. A monohydrate salt of compound according to Formula V,

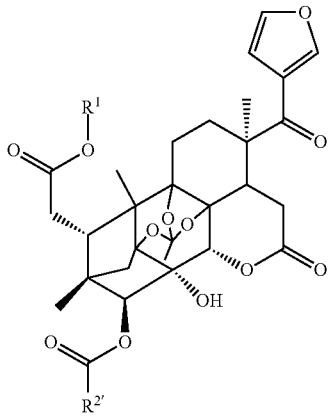

Formula V wherein $R^1$ is methyl,
wherein R2' is a straight, branched or cyclic optionally substituted alkyl group with 1 to 6 carbon atoms.

8. A compound according to Formula V,

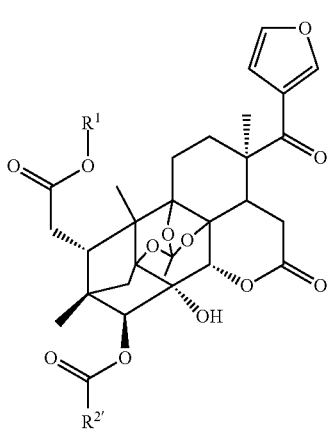

Formula V wherein $R^1$ is a straight, branched or cyclic alkyl group with 1 to 6 carbon atoms that is unsubstituted or substituted with the proviso that $R^1$ is not hydrogen, methyl or ethyl,
wherein R2' is a straight, branched or cyclic optionally substituted alkyl group with 1 to 6 carbon atoms.

9. The compound of claim 1, wherein $R^1$ is a straight, branched or cyclic alkyl group with 1 to 6 carbon atoms that is unsubstituted.

10. The compound of claim 1, wherein $R^1$ is a straight, branched or cyclic alkyl group with 1 to 6 carbon atoms that is substituted with —OH or a halogen.

11. The compound of claim 4, wherein $R^1$ is a straight, branched or cyclic alkyl group with 1 to 6 carbon atoms that is unsubstituted.

12. The compound of claim 4, wherein $R^1$ is a straight, branched or cyclic alkyl group with 1 to 6 carbon atoms that is substituted with —OH or a halogen.

* * * * *

UNITED STATES PATENT AND TRADEMARK OFFICE
CERTIFICATE OF CORRECTION

| | |
|---|---|
| PATENT NO. | : 12,157,744 B2 |
| APPLICATION NO. | : 18/469860 |
| DATED | : December 3, 2024 |
| INVENTOR(S) | : Westman and Malmbert |

Page 1 of 2

It is certified that error appears in the above-identified patent and that said Letters Patent is hereby corrected as shown below:

In the Specification

At Column 1, Lines 39-51, Formula Ia – delete the structure shown and replace it with the following:

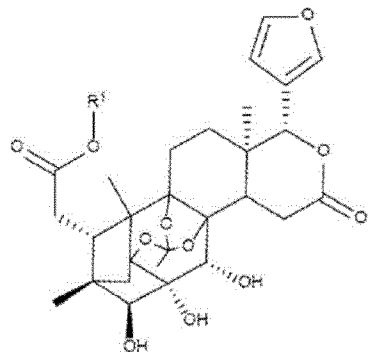

At Column 1, Lines 53-65, Formula Ib – delete the structure shown and replace it with the following:

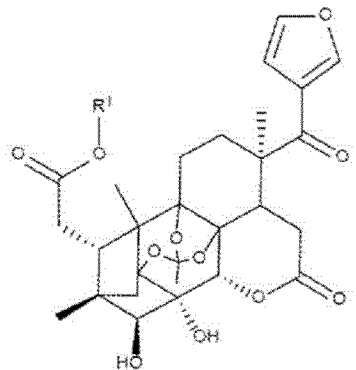

Signed and Sealed this
Eleventh Day of March, 2025

Coke Morgan Stewart
*Acting Director of the United States Patent and Trademark Office*

At Column 2, Lines 13-29, Formula IIa – delete the structure shown and replace it with the following:

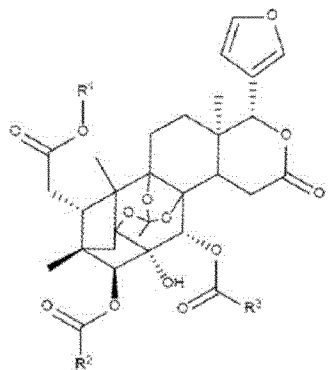

At Column 2, Lines 32-49, Formula IIb – delete the structure shown and replace it with the following:

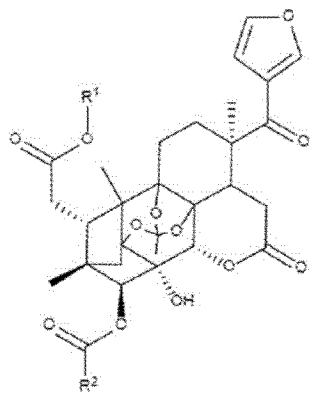

At Column 12, Line 24, delete "R1I", and insert --R1-- in its place.

In the Claims

In Claim 1, at Column 18, Line 62, insert --,-- after "straight".

In Claim 7, at Column 19, Line 62, delete "salt".

In Claim 7, at Column 19, Line 62, insert --the-- before "compound".